US00PP10963P

United States Patent [19]

Cheng et al.

[11] Patent Number: Plant 10,963

[45] Date of Patent: Jun. 22, 1999

[54] BIRCH TREE NAMED 'FARGO'

[75] Inventors: Zong-Ming Cheng; Dale E. Herman, both of Fargo, N. Dak.; Jeffrey P. Schnurr, Moscow, Id.; Arthur A. Boe, Faribault, Minn.

[73] Assignee: NDSU—Research Foundation, Fargo, N. Dak.

[21] Appl. No.: 08/923,964

[22] Filed: Sep. 5, 1997

[51] Int. Cl.[6] ..... A01H 5/00

[52] U.S. Cl. ..... Plt./216

[58] Field of Search ..... Plt./51.1

*Primary Examiner*—Elizabeth Kemmerer

*Attorney, Agent, or Firm*—Foley & Lardner

[57] ABSTRACT

A new and distinct cultivar of birch tree plant named 'Fargo', characterized by its distinctive narrow columnar growth habit, branching angles which average about 40° with the trunk; dark-green leaf color; bark color changes as tree matures; slightly exfoliating bark when mature; leaf retention into very late autumn; winter hardiness; high tolerance to wind; adaption to high-pH soil; above average resistance to the insect leaf miner; and high tolerance to drought and heat.

3 Drawing Sheets

The present invention comprises a new and distinct cultivar of birch tree, botanically known as *Betula platyphylla*, and hereinafter referred to by the cultivar name 'Fargo'.

BACKGROUND OF THE INVENTION

'Fargo' is a product of a planned breeding program which had the objective of creating a new cultivar of birch tree having improved horticultural characteristics, such as unique growth habit, enhanced hardiness, greener leaves, better adaptation to alkaline soil, and improved resistance/tolerance to insects. 'Fargo' was originated from an open-pollinated cross in a birch selection/breeding program at North Dakota State University, Fargo, ND, U.S.A. in 1986. The female parent was *Betula platyphylla* grown in North Dakota State University's Arboretum near Absaraka, ND. The arboretum was established by Dale E. Herman. The seeds were collected by Arthur A. Boe from a *Betula platyphylla* tree and sown in the Fall of 1986. The male parent of 'Fargo'is unknown. 'Fargo' was first noticed with upright growth habit from the progeny of the stated open-pollinated cross by Dale E. Herman in the Summer of 1989 in a field research plot in the West Campus of North Dakota State University, Fargo, ND. 'Fargo' was continuously observed by Arthur A. Boe until December 1992, and then by Zong-Ming Cheng until the present. The first act of asexual reproduction of 'Fargo' was accomplished by grafting to *B. platyphylla* rootsocks, then by micropropagation or tissue culture propagation by the inventors from the initial selection beginning in the Summer of 1992 in a controlled environment in Loftsgard Hall, Room 204, North Dakota State University, Fargo, ND. Horticultural examination of selected units has demonstrated that the combination of characteristics as herein disclosed for 'Fargo' are firmly fixed and are retained through successive generations of asexual reproduction. 'Fargo' has been observed in Fargo, ND; Mandan, ND; St. Paul, MN; and Saskatchewan, Canada since 1993 and characteristics have been stably maintained. 'Fargo' has not been evaluated under all possible environmental conditions. The phenotype may vary with variations in environment such as temperature, soil pH, rainfall, light intensity and day length, without a change in the genotype of the plant. The following observations, measurements and comparisons describe the plants grown in West Campus, North Dakota State University under natural field conditions which approximate those generally used in commercial practice.

BRIEF SUMMARY OF THE INVENTION

The following traits have been repeatedly observed and are determined to be basic characteristics of 'Fargo'which in combination distinguish this birch tree as a new and distinct cultivar.

1. Distinctive narrow columnar growth habit with branching angles average about 40°.
2. Dark green color of leaves (R.H.S 139A).
3. Bark colors change as the tree matures. The 3-year-old bark is grayish orange (R.H.S 165A), 6-year-old bark orange-white (R.H.S 159B), and mature trunk yellow-white (R.H.S 158C).
4. Slightly exfoliating bark when mature.
5. Leaves are retained on the tree very late in autumn, i.e., until the end of October in Fargo, ND.
6. Very winter-hardy (tolerate −39°C., wind chill −50°C. to −70°C.).
7. High tolerance to wind (no damage to wind up to 110 kilometers per hour).
8. Adaption to high-pH soil (pH 8.0).
9. Tolerates drought and heat.
10. Above average resistance to leaf miner.

Of the many commercial birch trees known to the applicants, the most similar in comparison to 'Fargo' is *Betula populifolia* 'Whitespire'. In comparison to 'Whitespire', 'Fargo' has a more columnar growth habit. 'Whitespire' has pyramidal growth habit with lateral branches that have a wider angle with the trunk than 'Fargo'.

BRIEF DESCRIPTION OF THE DRAWINGS

The accompanying color photographs show typical characteristics of 'Fargo', with the colors being as true as possible with illustrations of this type.

Sheet 1 is a side view of a specimen of 'Fargo' showing the columnar growth habit.

Sheet 2 shows the exfoliating bark.

Sheet 3 is a close-up of the male and female catkins.

DETAILED BOTANICAL DESCRIPTION

In the following description, color references are made to The R.H.S. (R.H.S) Colour Chart. The color values were determined between 10:00 a.m. and 2:00 p.m. in the Summer of 1995 under natural light at West Campus of North Dakota State University, Fargo, ND.

Classification:

*Botanical.*—*Betula platyphylla*.

*Commercial.*—'Fargo'.

Parentage:

*Origin.*—Plant grown in North Dakota State University Arboretum.

*Parentage.*—Seed parent: *Betula platyphylla*. Pollen parent: unknown.

Tree:

*Trunk.*—Multiple stem: Single-trunked tree. Size: Maximum diameter at age 10 is approximately 9.7 cm. Bark: Yellow-white (R.H.S 158C.), exfoliate slightly when mature. Thorns and spines: None.

*Branches.*—Angle of attachment: Average 39.5° based on measurement of 20 branches. Spacing: The crown has a maximum diameter of approximately 2.5 meters. Bark: Color changes with age, 3-year-old stem bark is grayish-orange (R.H.S 165S) and color of 6-year-old stem bark is orange-white (R.H.S 159B).

*Height.*—9.0–9.5 meters at 10 years of age.

*Growth habit or Form.*—Columnar, upright. *Growth rate.*—About 1–1.5 meters per year, depending on summer temperature and water availability.

*Foliage.*—Size of leaf: Length: 4–7 cm (average 5.7 cm). Width: 4.5–5.8 cm (average 5.2 cm). Shape of Leaf: Margin: Simple, alternate, ovate-cordate, with a rounded base, acuminate apices and serrate margins (about 5 serrations/cm).Texture: Smooth. Ribs and veins: 6–7 vein pairs per leaf. Pubescence distribution: Insignificant presence ence of pubescences. Color: Upper side: Dark green (R.H.S 139A). Petiole: 1.3–1.8 cm long, averaged 1.5 cm. Buds: intricate, pointed.

Catkins:

*Staminate.*—Shape: Pendulous, cylindrical. Size: 4–8 cm long, 0.5–1.0 cm wide (average 0.8 cm).

*Pistillate.*—Shape: Cylindrical. Size: 3.0–4.5 cm long (average 3.9 cm), 0.5–0.9 cm wide (average 0.7 cm).

*Timing of appearance of staminate and pistillate catkins.*—Male catkins develop during the summer and autumn and remain hanging in the tree through the winter; the female catkins appear from the leaf axils in spring (March–April in Fargo, ND).

*Timing of anthesis.*—May 1–15 in Fargo, depending on spring temperatures.

*Shape.*—Winged nutlet.

Insect and disease resistance: Above-average resistance to leaf miner (*Fenusa pusilla*) as compared with about 200 other trees in the research plot in Fargo, ND.

OTHER SIGNIFICANT CHARCTERISTICS.

1. Fast-growing 1–1.5 meters per year.

2. About 10% of the foliage is retained in tree throughout the winter.

What is claimed is:

1. A new and distinct cultivar of birch tree plant named 'Fargo', as illustrated and described.

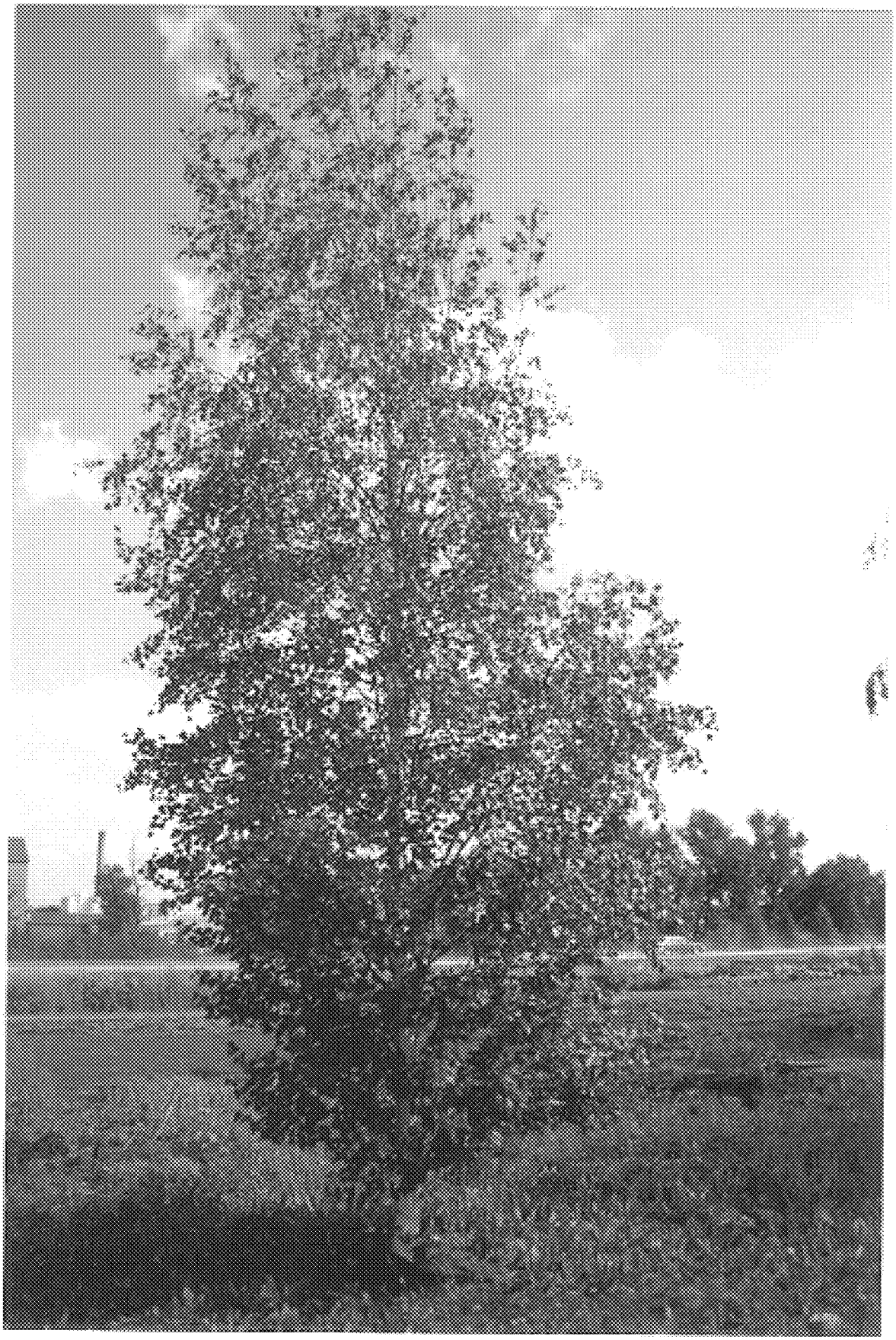

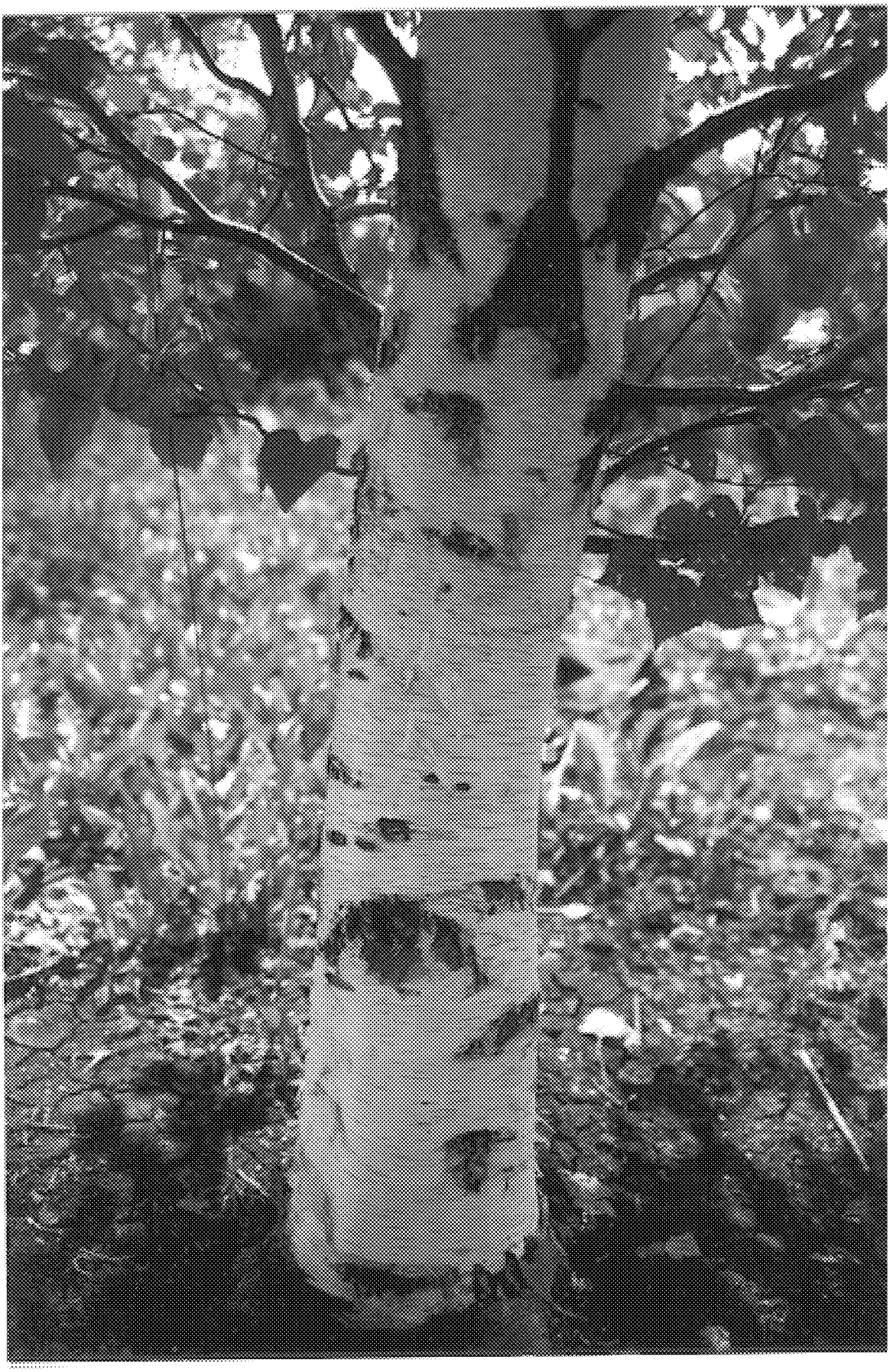

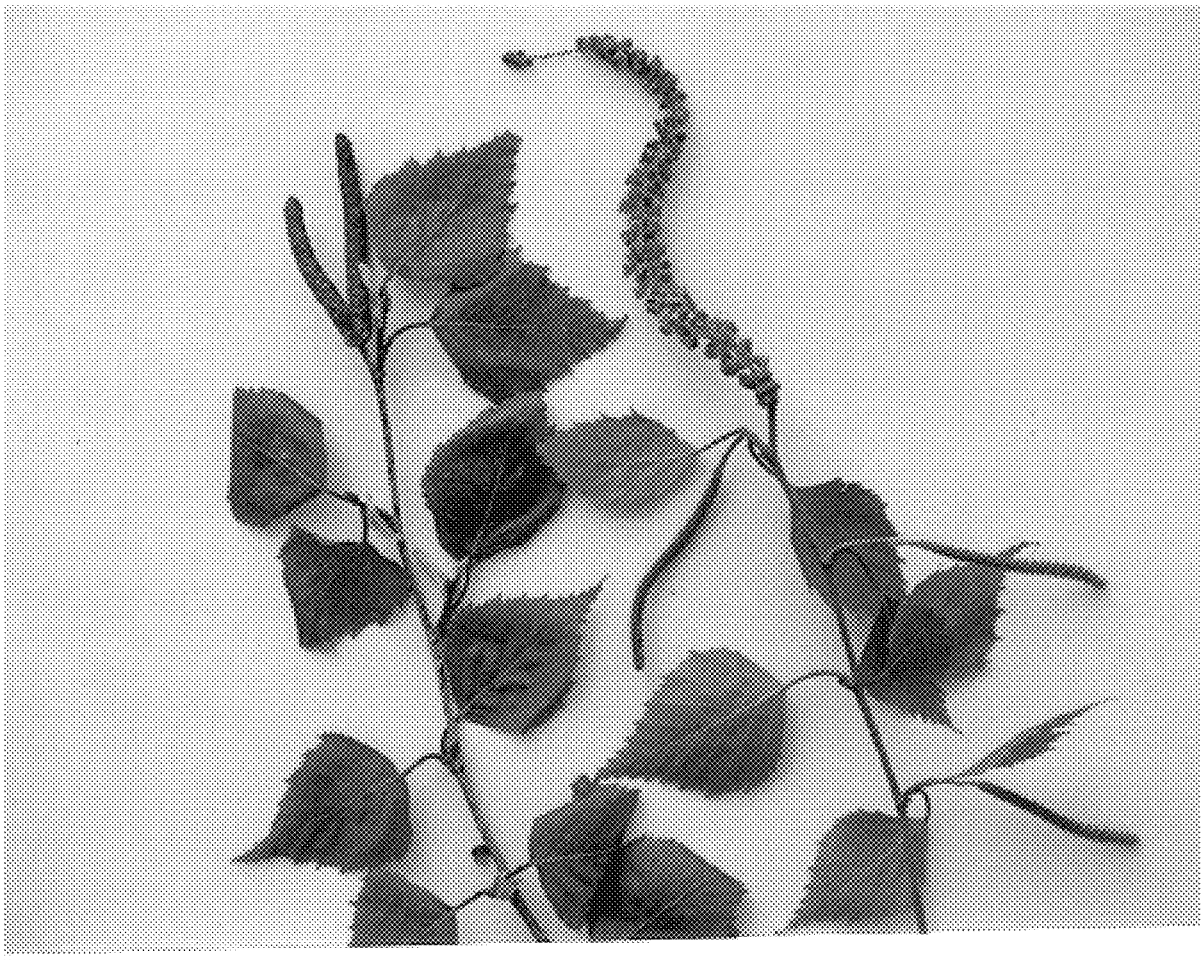

* * * * *